US 11,883,576 B2

United States Patent
Gerber et al.

(10) Patent No.: US 11,883,576 B2
(45) Date of Patent: Jan. 30, 2024

(54) PERITONEAL DIALYSIS INTRACYCLE OSMOTIC AGENT ADJUSTMENT

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Mozarc Medical US LLC, Minneapolis, MN (US)

( * ) Notice: Subject to any disclaimer, the term of this patent is extended or adjusted under 35 U.S.C. 154(b) by 697 days.

(21) Appl. No.: 17/024,039

(22) Filed: Sep. 17, 2020

(65) Prior Publication Data
US 2021/0001031 A1 Jan. 7, 2021

Related U.S. Application Data

(63) Continuation of application No. 15/666,631, filed on Aug. 2, 2017, now Pat. No. 10,874,790.
(Continued)

(51) Int. Cl.
*A61M 1/28* (2006.01)
*A61K 31/7004* (2006.01)
(Continued)

(52) U.S. Cl.
CPC ......... *A61M 1/282* (2014.02); *A61K 31/7004* (2013.01); *A61K 31/718* (2013.01);
(Continued)

(58) Field of Classification Search
CPC .............. A61M 1/282; A61M 1/1656; A61M 2202/0486; A61M 2205/3344;
(Continued)

(56) References Cited

U.S. PATENT DOCUMENTS 3,602,222 A   8/1971   Herndon
3,608,729 A   9/1971   Haselden
(Continued)

FOREIGN PATENT DOCUMENTS

CN   1273535           11/2000
CN   1643368 A         7/2005
(Continued)

OTHER PUBLICATIONS

Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.
(Continued)

*Primary Examiner* — Amber R Stiles

(57) ABSTRACT

The invention relates to systems and methods for making intracycle adjustments to an osmotic agent concentration of peritoneal dialysate inside the peritoneal cavity of a patient. The systems and methods include osmotic agent sources, flow paths, and processors to adjust the osmotic agent concentration of dialysate in the peritoneal cavity of the patient. The method can include infusing peritoneal dialysate containing an osmotic agent into the peritoneal cavity of a patient; monitoring one or more patient parameters; and adjusting the osmotic agent concentration of the peritoneal dialysate in the peritoneal cavity of the patient by infusing a concentrated osmotic agent solution or by infusing sterile fluid into the peritoneal cavity of the patient using an on-line peritoneal dialysis machine. The system can include a peritoneal dialysis cycler.

18 Claims, 3 Drawing Sheets

Related U.S. Application Data

(60) Provisional application No. 62/373,228, filed on Aug. 10, 2016.

(51) Int. Cl.
    *A61K 31/718* (2006.01)
    *A61M 1/16* (2006.01)

(52) U.S. Cl.
    CPC ... *A61M 1/1656* (2013.01); *A61M 2202/0486* (2013.01); *A61M 2205/3344* (2013.01); *A61M 2205/50* (2013.01); *A61M 2230/30* (2013.01)

(58) Field of Classification Search
    CPC .......... A61M 2205/50; A61M 2230/30; A61M 2230/005; A61M 1/28; A61M 1/287; A61K 31/7004; A61K 31/718
    See application file for complete search history.

(56) References Cited

U.S. PATENT DOCUMENTS

| | | |
|---|---|---|
| 3,669,878 A | 6/1972 | Marantz |
| 3,669,880 A | 6/1972 | Marantz |
| 3,730,183 A | 5/1973 | Goldsmith |
| 3,754,867 A | 8/1973 | Guenther |
| 3,850,835 A | 11/1974 | Marantz |
| 3,884,808 A | 5/1975 | Scott |
| 3,989,622 A | 11/1976 | Marantz |
| 3,989,625 A | 11/1976 | Mason |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,661,246 A | 4/1987 | Ash |
| 4,678,408 A | 7/1987 | Mason |
| 4,685,903 A | 8/1987 | Cable |
| 4,747,822 A | 5/1988 | Peabody |
| 4,750,494 A | 6/1988 | King |
| 4,772,560 A | 9/1988 | Attar |
| 4,799,493 A | 1/1989 | DuFault |
| 4,826,663 A | 5/1989 | Alberti |
| 4,828,693 A | 5/1989 | Lindsay |
| 4,976,683 A | 12/1990 | Gauthier |
| 5,032,265 A | 7/1991 | Jha |
| 5,080,653 A | 1/1992 | Voss |
| 5,091,642 A | 2/1992 | Chow |
| 5,092,838 A | 3/1992 | Faict |
| 5,092,886 A | 3/1992 | Dobos-Hardy |
| 5,097,122 A | 3/1992 | Coiman |
| 5,127,404 A | 7/1992 | Wyborny |
| 5,141,493 A | 8/1992 | Jacobsen |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,507,723 A | 4/1996 | Keshaviah |
| 5,643,201 A | 7/1997 | Peabody |
| 5,651,893 A | 7/1997 | Kenley |
| 5,683,432 A | 11/1997 | Goedeke |
| 5,744,031 A | 4/1998 | Bene |
| 5,762,782 A | 6/1998 | Kenley |
| 5,819,007 A | 10/1998 | Elghazzawi |
| 5,902,336 A | 5/1999 | Mishkin |
| 5,944,684 A | 8/1999 | Roberts |
| 5,987,352 A | 11/1999 | Klein |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,609,023 B1 | 8/2003 | Fischell |
| 6,627,164 B1 | 9/2003 | Wong |
| 6,645,191 B1 | 11/2003 | Knerr |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,726,647 B1 | 4/2004 | Sternby |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,131,956 B1 | 11/2006 | Pirazzoli |
| 7,175,809 B2 | 2/2007 | Gelfand |
| 7,207,946 B2 | 4/2007 | Sirokman |
| 7,208,092 B2 | 4/2007 | Micheli |
| 7,276,042 B2 | 10/2007 | Polaschegg |
| 7,399,289 B2 | 7/2008 | Gelfand |
| 7,404,799 B1 | 7/2008 | Koh |
| 7,500,958 B2 | 3/2009 | Asbrink |
| 7,566,432 B2 | 7/2009 | Wong |
| 7,575,564 B2 | 8/2009 | Childers |
| 7,610,086 B1 | 10/2009 | Ke |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,775,986 B2 | 8/2010 | Roeher |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,000,000 B2 | 8/2011 | Greenberg |
| 8,034,161 B2 | 10/2011 | Gura |
| 8,070,709 B2 | 12/2011 | Childers |
| 8,096,969 B2 | 1/2012 | Roberts |
| 8,105,260 B2 | 1/2012 | Tonelli |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |
| 8,409,441 B2 | 4/2013 | Wilt |

(56) References Cited

U.S. PATENT DOCUMENTS

| | | |
|---|---|---|
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,926,542 B2 | 1/2015 | Gerber |
| 9,700,663 B2 | 7/2017 | Burbank |
| 9,907,897 B2 | 3/2018 | Burbank |
| 10,046,100 B2 | 8/2018 | Burbank |
| 2002/0016550 A1 | 2/2002 | Sweeney |
| 2002/0042561 A1 | 4/2002 | Schulman |
| 2002/0112609 A1 | 8/2002 | Wong |
| 2003/0028089 A1 | 4/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | Thong |
| 2004/0019312 A1 | 1/2004 | Childers |
| 2004/0060865 A1 | 4/2004 | Callan |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0214863 A1 | 9/2005 | McDevitt |
| 2005/0234354 A1 | 10/2005 | Rowlandson |
| 2005/0234357 A1 | 10/2005 | Xue |
| 2005/0234381 A1 | 10/2005 | Niemetz |
| 2005/0234534 A1 | 10/2005 | Rowlandson |
| 2005/0236330 A1 | 10/2005 | Nier |
| 2005/0265895 A1 | 12/2005 | Kopelman |
| 2005/0274658 A1 | 12/2005 | Rosenbaum |
| 2006/0025661 A1 | 2/2006 | Sweeney |
| 2006/0025748 A1 | 2/2006 | Ye |
| 2006/0217771 A1 | 2/2006 | Soykan |
| 2006/0058731 A1 | 3/2006 | Burnett |
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0038138 A1 | 2/2007 | Gill |
| 2007/0066928 A1 | 3/2007 | Lannoy |
| 2007/0073168 A1 | 3/2007 | Zhang |
| 2007/0138011 A1 | 6/2007 | Hofmann |
| 2007/0161113 A1 | 7/2007 | Ash |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2007/0276270 A1 | 11/2007 | Tran |
| 2008/0006570 A1 | 1/2008 | Gura |
| 2008/0015487 A1 | 1/2008 | Szamosfalvi |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0200866 A1 | 8/2008 | Prisco |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0036825 A1 | 2/2009 | Petersen |
| 2009/0101577 A1 | 4/2009 | Fulkerson |
| 2009/0124869 A1 | 5/2009 | Hu |
| 2009/0124963 A1 | 5/2009 | Hogard |
| 2009/0127193 A1 | 5/2009 | Updyke |
| 2009/0149776 A1 | 6/2009 | Adams |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010425 A1 | 1/2010 | Yu |
| 2010/0010429 A1 | 1/2010 | Childers |
| 2010/0042035 A1 | 2/2010 | Moissl |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2010/0312172 A1 | 12/2010 | Hoffman |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0077575 A1 | 3/2011 | Kraemer |
| 2011/0079558 A1 | 4/2011 | Raimann |
| 2011/0081728 A1 | 4/2011 | Putnam |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0029937 A1 | 2/2012 | Neftel |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Soykan |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |

(56) References Cited

U.S. PATENT DOCUMENTS

| | | |
|---|---|---|
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan |
| 2013/0037465 A1 | 2/2013 | Heyes |
| 2013/0062265 A1 | 3/2013 | Balschat |
| 2013/0116578 A1 | 5/2013 | An |
| 2013/0158461 A1 | 6/2013 | Sasaki |
| 2013/0168316 A1 | 7/2013 | Noguchi |
| 2013/0186759 A1* | 7/2013 | Lin .................. B01D 61/58 204/520 |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0314625 A1 | 10/2014 | Clift |
| 2015/0032023 A1 | 1/2015 | Soykan |
| 2015/0080682 A1 | 3/2015 | Gerber |
| 2015/0088047 A1 | 3/2015 | Gerber |
| 2015/0141512 A1 | 5/2015 | Kizhakkedathu |
| 2015/0144539 A1 | 5/2015 | Pudil |
| 2015/0148697 A1 | 5/2015 | Burnes |
| 2015/0149096 A1 | 5/2015 | Soykan |
| 2015/0250427 A1 | 9/2015 | Soykan |
| 2015/0343126 A1 | 12/2015 | Merchant |
| 2015/0352269 A1 | 12/2015 | Gerber |
| 2015/0367054 A1 | 12/2015 | Gerber |
| 2016/0018347 A1 | 1/2016 | Drbal |
| 2016/0143774 A1 | 5/2016 | Burnett |
| 2016/0166753 A1 | 6/2016 | Meyer |
| 2016/0206801 A1 | 7/2016 | Gerber |
| 2016/0331884 A1 | 11/2016 | Sigg |
| 2017/0281848 A1* | 10/2017 | Axelsson .............. A61M 1/287 |
| 2017/0319768 A1 | 11/2017 | Szpara |
| 2018/0043080 A1 | 2/2018 | Gerber |

FOREIGN PATENT DOCUMENTS

| | | |
|---|---|---|
| CN | 101193667 | 6/2008 |
| CN | 101300476 A | 11/2008 |
| CN | 201342127 | 11/2009 |
| CN | 202048893 | 3/2011 |
| CN | 103037917 | 4/2013 |
| CN | 103394139 | 11/2013 |
| CN | 103619372 | 3/2014 |
| CN | 103717132 | 9/2014 |
| CN | 104174077 | 12/2014 |
| CN | 104833635 A | 8/2015 |
| CN | 104884102 | 9/2015 |
| CN | 105008893 B | 10/2015 |
| CN | 105142692 | 12/2015 |
| CN | 205672288 | 11/2016 |
| CN | 107206147 | 9/2017 |
| DE | 3224823 | 1/1984 |
| EP | 0266795 A2 | 11/1987 |
| EP | 0402505 | 12/1990 |
| EP | 0272414 | 10/1991 |
| EP | 0330892 | 7/1994 |
| EP | 1175238 | 11/2000 |
| EP | 1085295 | 11/2001 |
| EP | 1281351 | 2/2003 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| EP | 1582226 | 1/2016 |
| JP | S55138462 | 10/1980 |
| JP | S63-143077 | 11/1987 |
| JP | 2002533170 | 10/2002 |
| JP | 2002542900 | 12/2002 |
| JP | 2003235965 | 8/2003 |
| JP | 2005-533573 | 11/2005 |
| JP | 5-99464 | 10/2012 |
| WO | 1995003839 | 2/1995 |
| WO | WO 1998054563 | 12/1998 |
| WO | WO1999006082 | 2/1999 |
| WO | 9937342 | 7/1999 |
| WO | PCT1124599 | 5/2000 |
| WO | 0057935 | 10/2000 |
| WO | WO2000057935 A1 | 10/2000 |
| WO | 2000066197 | 11/2000 |
| WO | 200170307 A1 | 9/2001 |
| WO | 2001085295 A2 | 9/2001 |
| WO | 0185295 A2 | 11/2001 |
| WO | 2002013691 | 2/2002 |
| WO | WO 20020053211 | 7/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005033701 | 4/2005 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | WO2009094035 A1 | 1/2008 |
| WO | 2008037410 | 4/2008 |
| WO | 2009026603 | 12/2008 |
| WO | 2009024566 | 2/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | WO2009154955 A2 | 12/2009 |

(56) References Cited

FOREIGN PATENT DOCUMENTS

| | | |
|---|---|---|
| WO | WO 20090154955 | 12/2009 |
| WO | WO 20100002830 | 1/2010 |
| WO | 2010024963 | 3/2010 |
| WO | 2010028860 | 3/2010 |
| WO | 2010033314 | 3/2010 |
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | WO2013022760 A1 | 8/2011 |
| WO | WO 2011/132046 | 10/2011 |
| WO | 2011137693 | 11/2011 |
| WO | WO2011161056 | 12/2011 |
| WO | 2012042323 | 4/2012 |
| WO | 2012050781 | 4/2012 |
| WO | 2012051996 | 4/2012 |
| WO | 2012073420 | 7/2012 |
| WO | WO 2012/129501 | 9/2012 |
| WO | 2012148781 | 11/2012 |
| WO | 2012148784 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | WO2012148788 A1 | 11/2012 |
| WO | WO 20120148784 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | WO2014121161 | 8/2014 |
| WO | WO 20140121161 | 8/2014 |
| WO | WO 20140121169 | 8/2014 |
| WO | WO2015081221 A1 | 6/2015 |
| WO | WO 20150130205 | 9/2015 |
| WO | WO 20150159280 | 10/2015 |
| WO | WO2016049542 | 3/2016 |
| WO | WO-2016080883 A1 * | 5/2016 ............ A61M 1/28 |
| WO | WO 20160080883 | 5/2016 |
| WO | WO 20170034452 | 3/2017 |
| WO | WO 2017/176687 | 10/2017 |
| WO | WO 2017/176701 | 10/2017 |
| WO | WO2018229125 | 12/2018 |

OTHER PUBLICATIONS

Written Opinion in Dutch App. No. 2018577, dated Nov. 2, 2017.
European Search Report for App. No. 20198933.2, dated Dec. 22, 2020.
Brynda, et. al., The detection of toman 2-microglcbuiin by grating coupler immunosensor with three dimensional antibody networks. Biosensors & Bioelectronics, 1999, 363-368, 14(4).
Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
Zhong, et. al., Miniature urea sensor based on H(+)-ion sensitive field effect transistor and its application in clinical analysis, Chin. J. Biotechnol., 1992, 57-65. 8(1).
PCT/US2012/034331, International Search Report and Written Opinion dated Jul. 9, 2012.
Roberts M, The regenerative dialysis (REDY) sorbent system. Nephrology, 1998, 275-278:4.
U.S. Appl. No. 61/480,544, dated Apr. 29, 2011.
U.S. Appl. No. 61/480,541 dated Apr. 29, 2011.
Hemametrics, Crit-Line Hematocrit Accuracy, 2003, 1-5, vol. 1, Tech Note No. 11 (Rev. D).
Weissman, S., et al., Hydroxyurea-induced hepatitis in human immunodeficiency virus-positive patients. Clin. Infec. Dis, (Jul. 29, 1999): 223-224.
PCT/US2012/034334, International Search Report, dated Jul. 6, 2012.
PCT/US2012/034335, International Search Report, dated Sep. 5, 2012.
PCT/US/2012/034327, International Search Report, dated Aug. 13, 2013.
PCT/US/2012/034329, International Search Report, dated Dec. 3, 2012.
Foley, et al., Long Interdialytic Interval and Martality among Patients Receiving Hemodialysis, N Engl Jrnl Med. 2011:365(12):1099-1107.
PCT International Search Report from International Application No. PCT/US2014/067650, dated Mar. 9, 2015.
Wang, Fundamentals of intrathoracic impedance monitoring in heart failure, Am. J. Cardiology, 2007, 3G-10G: Suppl.
PCT/US2014/067650 International Search Report Written Opinion dated Mar. 9, 2015.
Bleyer, et al, Kidney International. Jun. 2006; 69(12):2268-2273.
Bleyer, et. al., Sudden and cardiac death rated in hemodialysis patients, Kidney International. 1999, 1553-1559: 55.
PCT/US2012/034335, International Preliminary Report on Patentability, dated Oct. 29, 2013.
PCT/US2012/034303, Internationa Search Report, dated Jul. 6, 2013.
PCT/US2012/034332, Internatonal Preliminary Report on Patentability, dated Oct. 29, 2013.
PCT/US2012/034333, International Preliminary Report on Patentability, dated Oct. 29, 2013.
PCT/US2012/034333, International Search Report, dated Aug. 29, 2012.
PCT/US2012/034327, International Preliminary Report on Patentability, dated Oct. 29, 2013.
PCT/US2012/034330, International Preliminary Report on Patentability, dated Oct. 29, 2013.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
U.S. Appl. No. 13/757,722, filed Feb. 1, 2013.
U.S. Appl. No. 13/757,794, filed Feb. 2, 2012.
U.S. Appl. No. 13/791,755, filed Mar. 8, 2013.
U.S. Appl. No. 13/424,479, filed Nov. 1, 2012.
U.S. Appl. No. 13/757,792, filed Feb. 2, 2013.
U.S. Appl. No. 13/757,794, filed Feb. 2, 2013.
U.S. Appl. No. 13/837,287, filed Mar. 15, 2013.
U.S. Appl. No. 13/424,429, filed Nov. 1, 2012.
Redfield, et. al, Restoration of renal response to atria! natriuretic factor in experimental low-output heat failure, Am. J. Physiol., Oct. 1, 1989, R917-923:257.
Rogoza, et. al., Validation of A&D UA-767 device for the self-measurement of blood pressure, Blood Pressure Monitoring, 2000, 227-231, 5(4).
PCT/US2012/034329, International Preliminary Report on Patentability, dated Oct. 29, 2013.
Lima, et. al., An electrochemical sensor based on nanostructure hollandite-type manganese oxide for detection of potassium ion, Sensors, Aug. 24, 2009, 6613-8625, 9.

(56) References Cited

OTHER PUBLICATIONS

Maclean, et, al., Effects of hindlimb contraction on pressor and muscle interstitial metabolite responses in the cat, J. App. Physiol., 1998, 1583-1592, 85(4).
U.S. Appl. No. 13/757,693, filed Feb. 1, 2013.
PCT Application, PCT/US2013/020404, filed Jan. 4, 2013.
U.S. Appl. No. 13/424,525, published Nov. 1, 2012.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2014/014357 International Search Report and Written Opinion dated May 19, 2014.
Ronco et al. 2008, Cardiorenal Syndrome, Journal American College Cardiology, 52:1527-1539, Abstract.
Overgaard, et. al., Activity-induced recovery of excitability in K+-depressed rat soleus muscle, Am. J. P 280: R48-R55, Jan. 1, 2001.
Overgaard. et. al., Relations between excitability and contractility in rate soleusmuscle: role of the NA+-K+ pump and NA+-K-S gradients. Journal of Physiology, 1999, 215-225, 518(1).
Zoccali, Pulmonary Congestion Predicts Cardiac Events and Mortality in ESRD, Clinical Epidemiology, J. Am Soc Nephrol 24:639-646, 2013.
Coast, et al. 1990, An approach to Cardiac Arrhythmia analysis Using Hidden Markov Models, IEEE Transactions on Biomedical Engineering. 1990, 37(9):826-835.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
U.S. Appl. No. 61/480,532, filed Apr. 29, 2011.
U.S. Appl. No. 13/424,479, published Nov. 1, 2012.
U.S. Appl. No. 13/424,525, published Nov. 1, 2013.
U.S. Appl. No. 61/480,530, filed Apr. 29, 2011.
U.S. Appl. No. 61/480,528, filed Apr. 29, 2011.
Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report dated May 26, 2015.
Genovesi, et al., Nephrology, Dialysis, Transplantation 2009; 24(8):2529-2536.
Secemsky, et. al, High prevalence of cardiac autonomic dysfunction and T-wave alternans in dialysis patients. Heart Rhythm, Apr. 2011, 592-598 : vol. 8, No. 4.
U.S. Appl. No. 13/424,517 IDS, filed Aug. 2, 2012.
U.S. Appl. No. 13/424,517, IDS filed Dec. 2, 2013.
Wei, et. al., Fullerene-cryptand coated piezoelectric crystal urea sensor based on urease, Analytica Chimica Acta, 2001,77-85:437.
Gambro AK 96 Dialysis Machine Operators Manual, Dec. 2012. p. 1-140.
Gambro AK 96 Dialysis Machine Operators Manual, Dec. 2012. p. 141-280.
Gambro AK 96 Dialysis Machine Operators Manual, Dec. 2012. p. 281-420.
Gambro AK 96 Dialysis Machine Operators Manual, Dec. 2012. p. 421-534.
U.S. Appl. No. 13/368,225, filed Feb. 7, 2012.
Leifer et al., A Study on the Temperature Variation of Rise Velocity for Large Clean Bubbles, J. Atmospheric & Oceanic Tech., vol. 17, pp. 1392-1402, Oct. 2000.

Talaia, Terminal Velocity of a Bubble Rise in a Liquid Column, World Acad. of Sci., Engineering & Tech., vol. 28, pp. 264-268, Published Jan. 1, 2007.
The FHN Trial Group. In-Center. Hemodialysis Six Times per Week versus Three Times per Week, New England Journal of Medicine, 2010 Abstract.
PCT/US2012/034332, International Search Report, dated Jul. 5, 2012.
Siegenthaler, et al., Pulmonary fluid status monitoring with intrathoracic impedance, Journal of Clinical Monitoring and Computing, 24:449-451, published Jan. 12, 2011.
Office Action in U.S. Appl. No. 13/757,792 dated Apr. 6, 2015.
U.S. Appl. No. 61/480,544. unpublished.
Office Action in U.S. Appl. No. 13/424,525 dated Aug. 11, 2015.
Office Action in U.S. Appl. No. 13/424,525 dated Oct. 20, 2016.
John Wm Agar: Review: Understanding sorbent dialysis systems, Nephrology, vol. 15, No. 4, Jun. 1, 2010, pp. 406-411.
European Office Action in Application 12717020.7 dated Sep. 14, 2016.
Office Action in U.S. Appl. No. 14/554,272 dated Aug. 8, 2016.
Office Action in U.S. Appl. No. 13/424,467 dated Oct. 16, 2013.
Office Action in U.S. Appl. No. 13/424,467 dated Mar. 3, 2014.
Office Action in U.S. Appl. No. 13/424,490 dated Oct. 22, 2013.
Office Action in U.S. Appl. No. 13/424,490 dated Mar. 10, 2014.
Office Action in U.S. Appl. No. 13/424,490 dated Jul. 14, 2014.
Office Action in U.S. Appl. No. 13/424,490 dated Dec. 5, 2014.
Office Action in U.S. Appl. No. 13/424,525 dated Sep. 29, 2014.
Office Action in U.S. Appl. No. 13/424,525 dated May 6, 2015.
Office Action in U.S. Appl. No. 13/424,454 dated Oct. 17, 2013.
Office Action in U.S. Appl. No. 13/424,454 dated Mar. 10, 2014.
Office action in U.S. Appl. No. 13/424,429 dated Oct. 15, 2015.
Office Action in U.S. Appl. No. 12/571,127 dated Feb. 27, 2014.
Office Action in U.S. Appl. No. 12/571,127 dated Jul. 6, 2015.
Office Action in U.S. Appl. No. 12/571,127 dated Dec. 17, 2015.
Office Action in U.S. Appl. No. 14/554,338 dated Jun. 7, 2016.
Office Action in U.S. Appl. No. 14/554,338 dated Sep. 28, 2016.
Office Action in U.S. Appl. No. 12/571,127 dated Nov. 8, 2012.
Office Action in U.S. Appl. No. 13/424,479 dated Oct. 25, 2014.
Office Action in U.S. Appl. No. 14/566,686 dated Apr. 28, 2016.
Office Action in Chinese Application No. 201510511657.9 dated Dec. 28, 2016.
U.S. Appl. No. 13/424,454, dated Nov. 1, 2012.
U.S. Appl. No. 13/424,467, published Nov. 1, 2012.
U.S. Appl. No. 13/424,533, dated Nov. 1, 2012.
Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
Gordhandas et al, Real-Time Extraction and Analysis of Key Morphological Features in the Electrocardiogram, for Data Compression and Clinical Decision Support, 2004, Computational Physiology, pp. 15-18.
European Office Action in Application 12717020.7 dated Dec. 11, 2015.
PCT/US2012/034331 International Preliminary Report on Patentability and Written Opinion dated Oct. 29, 2013.
Office Action in Chinese Application No. 201280020932.1 dated Jan. 7, 2015.
Office Action in Chinese Application No. 201280020932.1 dated Apr. 3, 2015.
U.S. Appl. No. 13/424,490, published Nov. 1, 2012.
U.S. Appl. No. 13/424,517, dated Nov. 1, 2012.
PCT/US2012/034330, International Search Report and Written Opinion dated Aug. 28, 2012.
Office Action in Chinese Application No. 201280020937.4 dated Mar. 22, 2016.
Office Action in Japanese Application No. 2014-508434 dated Nov. 16, 2015.
Office Action in Japanese Application No. 2014-508434 dated Dec. 8, 2014.
Office Action in Japanese Application No. 2014-508434 dated Nov. 4, 2016.

(56) References Cited

OTHER PUBLICATIONS

Office Action in European Application No. 12717019.9 dated Feb. 16, 2017.
Office Action in Chinese Application No. 201510511657.9 dated May 10, 2017.
PCT/US2014/065201 International Preliminary Report on Patentability dated May 19, 2016.
Office Action in European Application No. EP 12717021.5 dated Feb. 3, 2017.
Office Action in Chinese Application No. 201510593695.3 dated Jul. 12, 2017.
Office Action in European Application No. EP 12719170.8 dated Jan. 14, 2015.
Office Action in Japanese Application No. JP 2014-508437 dated Dec. 8, 2014.
U.S. Appl. No. 60/650,497, filed Feb. 7, 2005.
U.S. Appl. No. 61/480,539, filed Apr. 29, 2011.
U.S. Appl. No. 61/480,535, filed Apr. 29, 2011.
Nedelkov, et. al., Design of buffer exchange surfaces and sensor chips for biosensor chip mass spectrometry, Proteomics, 2002, 441-446, 2(4).
European Search Report App 14865374.4, dated Jun. 12, 2017.
European Search Report for Application No. 14865128.4 dated Jun. 20, 2017.
Green et al., Sudden Cardiac Death in Hemodialysis Patients: an In-Depth Review, Am J Kidney Dis 57(6)921:929; published Apr. 18, 2011.
Rajan et al. Generalized Feature Extraction for Time-Varying Autoregressive Models, IEEE Transacion Signal Processing vol. 44, No. 10; published Oct. 1, 1996.
Castellanos, et al, Clinical Relevance of Intraperitoneal Pressure in Peritoneal Dialysis Patients, Perit Dial Int. Sep.-Oct. 2017;37(5):562-567. doi: 10.3747/pdi.2016.00267. Epub Jul. 11, 2017.
Chinese OA in 201710669452.2 of Oct. 16, 2019.
Chinese Office Action for App. No. 201710669451.8, dated Jun. 2, 2020.
Chinese Office Action for App. No. 201710669451.8, dated Sep. 12, 2019.
Chinese Office Action for App. No. 201710669452.2, dated Dec. 3, 2019.
Chinese Office Action for App. No. 201710669454.1, dated Feb. 25, 2020.
Chinese Office Action for App. No. 201710669454.1, dated Jul. 3, 2020.
Chinese Office Action for App. No. 201710778666.3, dated Jul. 15, 2020.
Chinese Office Action for App. No. 201780019237.6, dated May 25, 2020.
Chinese Office Action for App. No. 201780019238.0, dated May 7, 2020.
Chinese Office Action for App. No. 201780019362.7, dated Jun. 2, 2020.
Chinese Office Action for App. No. 201811107614.4, dated Sep. 28, 2020.
Chinese Office Action for App. No. 2019071601874110, dated Jul. 19, 2019.
Chinese Office Action in App. No. 201480059332.5, dated Mar. 30, 2018.
Chinese Office Action in App. No. 201710669452.2, dated May 11, 2020.
Dejardin, et al, Intraperitoneal pressure in PD patients: relationship to intraperitoneal volume, body size and PD-related complications, Nephrol Dial Transplant. May 2007;22(5):1437-44.
European Office Action for App. No. 12719842.2, dated Jul. 15, 2020.
European Office Action for App. No. 14859115.9, dated Mar. 25, 2020.
European Office Action for App. No. 17718246.6, dated Apr. 2, 2020.
European Office Action for App. No. 17754582.9, dated Aug. 10, 2020.
European Search Report for App. No. 17185636.2, dated Mar. 27, 2018.
European Search Report for App. No. 14859115.9, dated Jan. 5, 2018.
European Search Report for App. No. 17185636.2 dated Jan. 10, 2018.
European Search Report for App. No. 17185638.8, dated Dec. 19, 2017.
European Search Report for App. No. 17185808.7, dated Jan. 2, 2018.
European Search Report for App. No. 17185810.3, dated Dec. 15, 2017.
European Search Report for App. No. 17190053.3, dated Jan. 2, 2018.
European Search Report for App. No. 17190066.5, dated Jan. 16, 2018.
European Search Report for App. No. 17190084.8, dated Feb. 9, 2018.
European search report for App. No. 19219612.9, dated Apr. 29, 2020.
F. Locatelli, et al: "Haemodialysis with on-line monitoring equipment: tools or toys?" Nephrology Dialysis Transplantation., vol. 20, No. 1, Jan. 1, 2005.
Heiko Hickstein, et al; "Clinical application of fuzzy-controlled blood pressure stabilization in patients prone to hypotension duirng hemodiaylsis", Dyalysis & Transplantation, vol. 38, No. 2, Feb. 1, 2009, pp. 58-64.
Henderson, et al, "Online Preparation of Sterile Pyrogen-Free Electrolyte Solution," Trans. Am. Soc. Artif.Intern.Organs, 1978 pp. 465-467.
Indian OA of Nov. 21, 2019 in 2981/KOLNP/2013.
International Preliminary Report on Patentability for App. No. PCT/US2019/019334, dated Jun. 12, 2019.
International Search Report for App. No. PCT/US2019/061670, dated Jan. 15, 2020.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
Office Action for EP App. No.17185808.7, dated Oct. 8, 2019.
Office Action for European App. No. 17718241.7, dated Apr. 2, 2020.
Office Action for European Application No. 17185636.2, dated Mar. 19, 2020.
Office Action in Chinese App. No. 201710778666.3 dated Sep. 19, 2019.
Office Action in Chinese App. No. 201780019238.0, dated Sep. 25, 2020.
PCT/US2016/058579 International Search Report dated Jan. 31, 2017.
PCT/US2016/058579 Written Opinion dated Jan. 31, 2017.
PCT/US2017/025868 International Search Report dated Jun. 29, 2017.
PCT/US2017/025868 Written Opinion dated Jun. 29, 2017.
PCT/US2017/030377 International Search Report dated Sep. 1, 2017.
PCT/US2017/030377 Written Opinion dated Sep. 1, 2017.
PCTUS20170146199 ISR and written opinion, dated Feb. 19, 2018.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.

\* cited by examiner

PERITONEAL DIALYSIS INTRACYCLE OSMOTIC AGENT ADJUSTMENT

CROSS-REFERENCE TO RELATED APPLICATIONS

This application is a Continuation of U.S. patent application Ser. No. 15/666,631 filed Aug. 2, 2017, which claims the benefit of and priority to U.S. Provisional Patent Application No. 62/373,228 filed Aug. 10, 2016, the entire disclosure of which is incorporated by reference herein.

FIELD OF THE INVENTION

The invention relates to systems and methods for making intracycle adjustments to an osmotic agent concentration of peritoneal dialysate inside the peritoneal cavity of a patient. The systems and methods include osmotic agent sources, flow paths, and processors to adjust the osmotic agent concentration of dialysate in the peritoneal cavity of the patient.

BACKGROUND

Peritoneal Dialysis (PD), including Automated Peritoneal Dialysis (APD) and Continuous Ambulatory Peritoneal Dialysis (CAPD), is a dialysis treatment that can be performed at home, either by a patient alone or with a caregiver. PD differs from Hemodialysis (HD) in that blood is not removed from the body and passed through a dialyzer, but rather a catheter is placed in the peritoneal cavity and dialysate introduced directly into the peritoneal cavity. Blood is cleaned inside the patient using the patient's own peritoneum as a type of dialysis membrane.

Osmotic agents in the peritoneal dialysate drive the movement of water from the blood of the patient into the peritoneal cavity for removal. The driving force for water movement is a function of the concentration of the osmotic agent in the peritoneum. Different osmotic agents provide different fluid removal profiles, with certain osmotic agents, such as dextrose, providing a high degree of fluid removal early in a cycle and other osmotic agents, such as icodextrine, providing slower fluid removal over a longer period of time. Use of dextrose in the peritoneal dialysate provides quick fluid removal, followed by a period of reduced fluid removal. However, known systems do not provide any mechanism to change or adjust the osmotic agent composition or concentration once the dialysate is infused into the patient to take advantage of the different fluid removal profiles.

Typical peritoneal dialysis cycles are between one and three hours long, or between one and four hours long in CAPD. The fluid is delivered to the peritoneum and allowed to dwell for given periods of time. During the dwell period, the glucose/dextrose osmotic agent can be transported to the patient's blood through the peritoneum and has an exponential decay in concentration within the peritoneum, meaning that the transport is very effective during the first portion of the cycle but then is much less efficient later in the cycle. As a result, high concentrations of glucose/dextrose may be needed to achieve the overall session goals. The high glucose/dextrose concentrations may cause acceleration of the peritoneum membrane wear out and subjecting the patient to more glucose/dextrose than may be need if the delivery was conducted in a more optimal manner. High glucose/dextrose concentrations can also lead to spikes in blood glucose resulting from the initial high glucose/dextrose concentration in the peritoneal dialysate. These spikes can be problematic for diabetic patients which include about 40-50% of chronic kidney disease patients.

Hence, there is a need for systems and methods that can make an intracycle adjustment to the osmotic agent concentration in the peritoneal cavity of the patient, by either increasing or decreasing the osmotic agent concentration during the dwell period, to increase transport effectiveness. The need extends to increasing transport effectiveness at any point during a cycle. There is a need for a system that can make the intracycle adjustments to reduce the overall number of cycles required for effective therapy or to reduce inefficiencies resulting from repeatedly filling and draining the peritoneal cavity. There is a further need for systems and methods to determine the optimal increase or decrease in osmotic agent concentration during the cycle.

SUMMARY OF THE INVENTION

The first aspect of the invention relates to a method for adjusting an osmotic agent concentration in a peritoneal cavity. In any embodiment, the method can include infusing peritoneal dialysate containing an osmotic agent into the peritoneal cavity of a patient; monitoring one or more patient parameters; and adjusting the osmotic agent concentration of the peritoneal dialysate in the peritoneal cavity of the patient by infusing a concentrated osmotic agent solution or by infusing sterile fluid into the peritoneal cavity of the patient using the on-line peritoneal dialysis machine.

In any embodiment, the method can include the step of infusing the concentrated osmotic agent solution into the patient mid-cycle. In any embodiment, the step of infusing the concentrated osmotic agent solution into the patient can occur at any time point during a cycle, e.g., $\frac{1}{16}$, $\frac{1}{8}$, $\frac{1}{4}$, $\frac{1}{2}$, $\frac{7}{8}$, $\frac{3}{4}$, $\frac{15}{16}$ of a cycle. In any embodiment, the method can include the step of infusing the sterile fluid into the peritoneal cavity of the mid-cycle. In any embodiment, the step of infusing the sterile fluid into the patient can occur at any time point during a cycle, e.g., $\frac{1}{16}$, $\frac{1}{8}$, $\frac{1}{4}$, $\frac{1}{2}$, $\frac{7}{8}$, $\frac{3}{4}$, $\frac{15}{16}$ of a cycle.

In any embodiment, the method can include the step of sterilizing the concentrated osmotic agent solution prior to infusing the concentrated osmotic agent solution into the peritoneal cavity of the patient.

In any embodiment, the method can include the step of draining a volume of peritoneal dialysate from the peritoneal cavity of the patient prior to the step of infusing the concentrated osmotic agent solution into the peritoneal cavity of the patient.

In any embodiment, the method can include the step of draining a volume of peritoneal dialysate from the peritoneal cavity of the patient prior to the step of infusing sterile fluid into the peritoneal cavity of the patient.

In any embodiment, the method can include the step of determining a change to the osmotic agent concentration based on one or more patient parameters prior to the step of adjusting the osmotic agent concentration.

In any embodiment, the patient parameters can be selected from the group of: blood pressure and intraperitoneal pressure.

In any embodiment, the method can include the steps of determining an intraperitoneal pressure at a first time and at least a second time, and wherein the step of determining a change to the osmotic agent concentration can include determining a change to the osmotic agent concentration based on a change in intraperitoneal pressure.

In any embodiment, the step of adjusting the osmotic agent concentration can include selectively flowing fluid from an osmotic agent source into the peritoneal cavity of the patient.

In any embodiment, the osmotic agent source can contain glucose/dextrose, icodextrin, or combinations thereof.

In any embodiment, the step of adjusting the osmotic agent concentration can include selectively flowing fluid from an osmotic agent source into the peritoneal cavity of the patient at a set time after infusing the peritoneal dialysate into the peritoneal cavity of the patient.

In any embodiment, the peritoneal dialysate can have multiple osmotic agents.

In any embodiment, the peritoneal dialysate can include icodextrin and glucose/dextrose.

In any embodiment, the method can include the steps of draining the peritoneal dialysate from the patient; and infusing a second peritoneal dialysate into the patient; wherein the second peritoneal dialysate has an osmotic agent different from the first peritoneal dialysate.

In any embodiment, the method can include receiving one or more dialysis results from at least one prior dialysis session into a machine readable storage medium; and receiving a dialysis prescription from the prior dialysis session into a machine readable storage medium; and the one or more dialysis results can include a volume of ultrafiltrate removed and a rate of ultrafiltration; and the dialysis prescription can include an adjustment made to the osmotic agent concentration in the peritoneal cavity of the patient during the prior dialysis session.

In any embodiment, the step of adjusting the osmotic agent concentration can include determining a change to the osmotic agent concentration based on the dialysis results from the prior dialysis session and the dialysis prescription from the prior dialysis session.

In any embodiment, the step of infusing a concentrated osmotic agent solution or sterile fluid can be performed at a set time after infusing the peritoneal dialysate into the peritoneal cavity of the patient.

In any embodiment, the steps of monitoring the one or more patient parameters and adjusting the osmotic agent concentration of the peritoneal dialysate can be performed by a processor.

In any embodiment, the patient parameters can be monitored while the peritoneal dialysate is inside the patient during a cycle.

The features disclosed as being part of the first aspect of the invention can be in the first aspect of the invention, either alone or in combination.

The second aspect of the invention is drawn to a system. In any embodiment, the system can include a peritoneal dialysis cycler having either a combined effluent and infusion line or an infusion line and an effluent line, the peritoneal dialysis cycler further having an infusion pump; a peritoneal dialysate generation flow path fluidly connected to the infusion line or combined effluent and infusion line; the peritoneal dialysate generation flow path having: (i) a water source fluidly connected to the peritoneal dialysate generation flow path; (ii) a concentrate source fluidly connected to the peritoneal dialysate generation flow path; (iii) at least a first osmotic agent source fluidly connected to the peritoneal dialysate generation flow path; (iv) an osmotic agent pump positioned on a fluid line between the osmotic agent source and the peritoneal dialysate generation flow path; and (v) a sterilization module positioned in the peritoneal dialysate generation flow path downstream of the osmotic agent source and concentrate source.

In any embodiment, the system can include a processor in communication with the osmotic agent pump and the infusion pump; the processor selectively controlling the osmotic agent pump and infusion pump to adjust an osmotic agent concentration in a peritoneal cavity of a patient.

In any embodiment, the processor can be in communication with at least one sensor; the processor adjusting the osmotic agent concentration based on data received from the at least one sensor.

In any embodiment, the sensor can be selected from the group of: a blood pressure sensor, and a pressure sensor.

In any embodiment, the system can include at least a second osmotic agent source, the first osmotic agent source and second osmotic agent source containing different osmotic agents.

The features disclosed as being part of the second aspect of the invention can be in the second aspect of the invention, either alone or in combination.

DETAILED DESCRIPTION OF THE INVENTION

Figure 1:
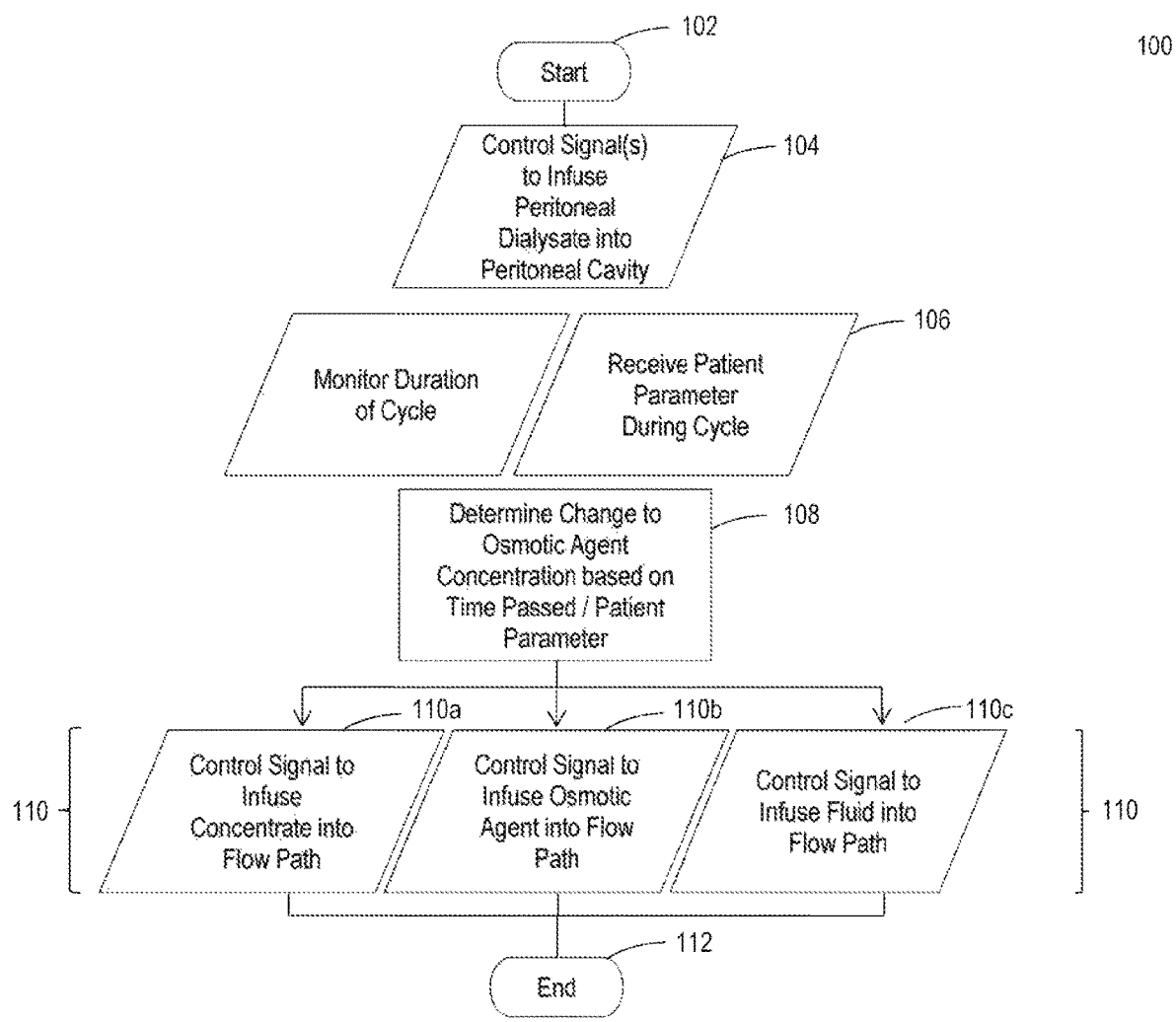
FIG. 1 shows a flow chart of a method for adjusting the osmotic agent concentration within the peritoneal cavity of a patient.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "adjusting" or to "adjust" a dialysis parameter refers to changing any parameter of a peritoneal dialysis session, including changing the concentration of one or more solutes, the temperature, the dwell time, and the number of cycles.

The term "blood pressure" refers to the pressure of blood in the body of a patient and can refer to systolic pressure, diastolic pressure, or a combination thereof.

The term "blood pressure sensor" refers to any sensor capable of determining the blood pressure of a patient. The blood pressure sensor can be implanted, wearable, or an external sensor.

The term "communication" refers to an electronic or wireless link between two components.

The term "comprising" includes, but is not limited to, whatever follows the word "comprising." Use of the term indicates the listed elements are required or mandatory but that other elements are optional and may be present.

A "concentrated osmotic agent solution" is a solution containing an osmotic agent in a concentration higher than that generally used in peritoneal dialysis.

A "concentrate source" is a source of one or more solutes. The concentrate source can have one or more solutes with a solute concentration greater than the solute concentration to be used for dialysis. The concentrate in the concentrate source can also be lower than the solute concentration generally used in dialysis for generation of low concentration dialysate.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "control," "controlling," or "controls" refers to the ability of one component to direct the actions of a second component.

The term "cycle" or "peritoneal dialysis cycle" refers to the infusion of peritoneal dialysate into a patient, a dwell of the peritoneal dialysate within the peritoneal cavity of the patient, and the removal of the peritoneal dialysate from the peritoneal cavity of the patient. The process of filling and then draining your abdomen can also be seen as an "exchange" used and clean fluids. However, the number, length, and timing of "cycles" or "exchanges" are non-limiting. For example, Continuous Ambulatory Peritoneal Dialysis (CAPD) and Continuous Cycling Peritoneal Dialysis (CCPD) may occur on different schedules, but the process of filling and then draining the peritoneal cavity can be referred to as "cycles" for both CAPD and CCPD. As such, the term is "cycle" or exchange refers to any particular type of dialysis schedule or type.

The terms "determining" and "determine" refer to ascertaining a particular state of a system or variable(s).

A "dialysis prescription" refers to the set parameters of a peritoneal dialysis session or cycle, including the concentration of one or more solutes in the dialysate, the temperature, the dwell time, the number of cycles in a session, or any intra-cycle adjustments made to the dialysate.

The term "dialysis results" refers to any variables measured as a result of dialysis therapy. The dialysis results can include patient variables, such as blood pressure or comfort, or can include therapy variables, such as an amount of ultrafiltrate removed, a rate of ultrafiltration, or any other results.

A "dialysis session" is a set of peritoneal dialysis cycles performed over a time period as part of ongoing therapy. The peritoneal dialysis session can last a day or more, and can include any number of cycles.

The term "downstream" refers to a position of a first component in a flow path relative to a second component wherein fluid will pass by the second component prior to the first component during normal operation. The first component can be said to be "downstream" of the second component, while the second component is "upstream" of the first component.

The term "draining" or to "drain" fluid refers to removing peritoneal dialysate from the peritoneal cavity of a patient.

The term "effluent line" refers to a fluid connector for removing fluid from a peritoneal cavity of a patient. The term effluent line can also refer to a combined effluent and infusion line.

The terms "fluidly connectable," "fluidly connected," "fluid connection" "fluidly connectable," or "fluidly connected" refer to the ability to pass fluid, gas, or mixtures thereof from one point to another point. The two points can be within or between any one or more of compartments, modules, systems, and components, all of any type.

The term "infusing peritoneal dialysate" or to "infuse peritoneal dialysate" refers to the movement of peritoneal dialysate into the peritoneal cavity of a patient An "infusion line" is a fluid line for carrying peritoneal dialysate into a body cavity or part of a patient such as a peritoneal cavity. The term "infusion line" can also refer to a combined effluent and infusion line.

An "infusion pump" is a pump configured to move fluid through an infusion line into the peritoneal cavity of a patient. The infusion pump can also drain fluid from the peritoneal cavity of the patient.

The term "intraperitoneal pressure" refers to the fluid pressure within the peritoneal cavity of a patient.

The term "machine-readable storage medium" refers to any electronic device capable of storing information in a digital format for reading by a computer, processor, or other electronic device.

The term "mid-cycle" refers to the time period between infusion of peritoneal dialysate into a patient and drainage of the peritoneal dialysate from the patient. As such, mid-cycle infusion of an osmotic agent can occur between the infusion of peritoneal dialysate into a patient and drainage of the peritoneal dialysate from the patient to adjust the present concentration of the osmotic agent in the peritoneum of the patient.

The term "monitoring" or to "monitor" refers to determining a status of a system or patient over time.

An "on-line peritoneal dialysis machine" is a set of components that generate peritoneal dialysate, infuse the peritoneal dialysate into a patient, and drain the peritoneal dialysate from the patient.

An "osmotic agent" is a substance dissolved in water capable of driving a net movement of water by osmosis across a semi-permeable membrane due to concentration differences of the osmotic agent on each side of the semi-permeable membrane.

The term "osmotic agent concentration" refers to the amount of an osmotic agent per unit volume of peritoneal dialysate.

The term "osmotic agent pump" refers to a pump configured to move fluid from an osmotic agent source into a peritoneal dialysate generation flow path.

An "osmotic agent source" refers to a source of osmotic agents in solid and/or solution form. The osmotic agent source can interface with at least one other module found in systems for dialysis. The osmotic agent source can contain at least one fluid pathway and include components such as conduits, valves, filters or fluid connection ports, any of which are fluidly connectable to each other or to a fluid flow path. The osmotic agent source can either be formed as a stand-alone enclosure or a compartment integrally formed with an apparatus for dialysis for containing an osmotic agent source. The osmotic agent concentration in the osmotic agent source can be lower or higher than the osmotic agent concentration generally used in dialysis for generation of low or high osmotic agent concentration dialysate.

A "patient" or "subject" is a member of any animal species, preferably a mammalian species, optionally a human. The subject can be an apparently healthy individual, an individual suffering from a disease, or an individual being treated for a disease.

The term "patient parameter" refers to any data without limitations that gives any medical relevant information about the health status of a patient. A patient physiological parameter can include, but is not limited to, blood pressure, blood solute levels, posture or any other medically relevant information. For example, the physiological parameters can encompasses information such as age, weight, gender, current drug therapies, smoking habits, diet, etc.

The term "peritoneal cavity" refers to a space between the parietal peritoneum and visceral peritoneum of a patient.

"Peritoneal dialysate" is a dialysis solution to be used in peritoneal dialysis having specified parameters for purity and sterility. Peritoneal dialysate is different than the dialysate used in hemodialysis, although peritoneal dialysate may be used in hemodialysis.

A "peritoneal dialysate generation flow path" is a path used in generating dialysate suitable for peritoneal dialysis.

The term "positioned" refers to the location of a component.

The term "pressure sensor" refers to any component capable of determining the force exerted by a fluid.

The term "processor" as used herein is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "pump" refers to any device that causes the movement of fluids or gases by applying suction or pressure.

The term "receiving" or to "receive" means to obtain information from any source.

The term "selectively flowing fluid" refers to operating a system to move fluid in a specified flow path.

A "sensor" is a component capable of determining one or more states of one or more variables in a system.

The term "set time" refers to a predetermined moment or time, or a predetermined amount of time between two events.

The term "sterile fluid" refers to a fluid having a level of chemical or biological contaminants lower than a predetermined safe level for infusion into a patient.

A "sterilization module" is a component or set of components to sterilize a fluid by removing or destroying chemical or biological contaminants.

"Sterilizing" or to "sterilize" refers to the process of removing or destroying chemical or biological contaminants in a fluid.

The term "ultrafiltrate" refers to fluid that is removed from a subject by convection through the peritoneal membrane during peritoneal dialysis.

The term "ultrafiltration," as used herein, refers to the fluid removal from blood during peritoneal dialysis by passing fluid through the peritoneal membrane.

The term "water source" refers to a source from which potable water can be obtained.

Intracycle Osmotic Agent Adjustments

FIG. 1 is a flowchart of a computer implemented method 100 for adjusting an osmotic agent concentration in a peritoneal cavity of a patient. The method can be performed using a system programmed or constructed to adjust an osmotic agent concentration in a peritoneal cavity of a patient. The system can include a machine readable storage medium including instructions that, when executed by a dialysis machine, cause the dialysis machine and related components to perform any one of the methods.

The method 100 can begin in operation 102. A peritoneal dialysis session can be initiated (such as might occur before or during a first cycle of a session) or already underway (such as might occur before or during a subsequent cycle of a session).

In operation 104, control signals infusing an initial bolus of peritoneal dialysate fluid containing one or more osmotic agents, as well as other solutes, into the peritoneal cavity of a patient can be sent to components of the system. For example, a processor of the system can be in communication with a concentrate source and osmotic agent sources and can control the movement of fluid from the concentrate source and osmotic agent sources to a peritoneal dialysate generation flow path of the system. The processor of the system can control the movement of peritoneal dialysate into the peritoneal cavity through an integrated cycler, thereby delivering the initial bolus of fluid.

In operation 106, a parameter (such as time or a patient parameter) may be monitored. Multiple instances of operation 106 are depicted in operation 106. For example, in operation 106a, a duration of time passed since infusion of the peritoneal dialysate into the peritoneal cavity of the patient may be monitored. Additionally or alternatively, in operation 106b, one or more patient parameters may be received during a current cycle. For example, the processor of the system can monitor one or more patient parameters while the peritoneal dialysate is inside the peritoneal cavity during the current cycle. For example, a blood pressure of the patient may be sensed by a blood pressure sensor and monitored by the processor of the system to monitor for a hypotensive episode. Ultrafiltration at too high of a rate or in too high of a volume may lower the patient's blood pressure, placing the patient in a hypotensive state. Pressure sensors in the catheter of the cycler can determine the intraperitoneal pressure of the patient. One of skill in the art will understand that interabdominal pressure can alternatively or additionally be used to measure pressure. The intraperitoneal pressure can be monitored periodically and used as a surrogate to determine the ultrafiltrate volume at any time during a cycle. The changes in ultrafiltrate volume or ultrafiltration rate as determined by the pressure sensors can be extrapolated to determine the efficiency of the osmotic agent over any period of time. As the efficiency of the osmotic agent decreases, additional osmotic agent can be infused into the patient. One of ordinary skill in the art will recognize that multiple parameters can monitored. Table 1 contains illustrative examples of parameters and adjustments.

TABLE 1

| Patient Parameters | Osmotic Agent Adjustment |
|---|---|
| Blood pressure | Dilution of fluid |
| Intraperitoneal pressure | Osmotic agent concentration, dilution of fluid |
| Timing | Osmotic agent concentration |

Glucose/dextrose osmotic agents typically used in peritoneal dialysis can be transported to the patient's blood through the peritoneum and has an exponential decay in intraperitoneal concentration, meaning that the transport is very effective during the first portion of the cycle but then is much less efficient later in the cycle. By adding a concentrated osmotic agent solution into the peritoneal cavity of the patient during the dwell time, a lower initial osmotic agent concentration can be used.

In operation 108, a change in one or more osmotic agent concentrations may be determined based on the parameter monitored in operation 106. For example, a change in one or more osmotic agent concentrations may be determined based on the occurrence of the passage of a predetermined period of time. As another example, the processor of the system may calculate an adjustment to the osmotic agent concentration based on the monitored blood pressure.

In operation 110, one or more control signals may be sent to components of the system to adjust the osmotic agent concentration of the peritoneal dialysate in the peritoneal cavity of the patient by infusing a sterile fluid into the peritoneal cavity of the patient. Multiple instances of operation 110 are shown in FIG. 1. For example, in operation 110a, the processor of the system may selectively flow concentrate solution from one or more concentrate sources to the peritoneal dialysate generation flow path and into the patient. The concentrate can be diluted with water in the peritoneal dialysate generation flow path to provide a peritoneal dialysate with a predetermined solute concentration. Additionally or alternatively, the processor of the system may selectively flow of one or more osmotic agents from one or more osmotic agent sources to the peritoneal dialysate generation flow path and into the patient in operation 110b. By adding a concentrated osmotic agent solution during the cycle, the system can step up, or increase the effectiveness of fluid removal during the cycle. Increasing the intracycle effectiveness of fluid removal may reduce the number of overall cycles needed and reduce the inefficiencies of filling and emptying the peritoneal cavity, thus reducing the overall therapy time and/or improving the overall therapy. Additionally or alternatively, the processor of the system may selectively flow sterile fluid from, e.g., a water source to the peritoneal dialysate generation flow path and into the patient in operation 110c. If a hypotensive episode is detected in the patient, the system can lower the osmotic agent concentration in the peritoneal cavity by diluting the dialysate already in the peritoneal cavity with straight water or a cation solution that is close to isotonic. Additionally or alternatively, the processor of the system may control the movement of peritoneal dialysate into the peritoneal cavity of the patient through an infusion line, both during infusion of the initial bolus of fluid, and during the addition of a subsequent bolus of fluid delivered during the cycle (i.e., during the current dwell portion of the cycle).

In operation 112, the method 110 may end. One of ordinary skill in the art will recognize that the method of FIG. 1 may loop during a particular cycle and/or session. In one embodiment, the system may employ a learning mode. During the session monitored, various osmotic agent adjustments and parameters (e.g., time and patient parameters) may be monitored and recorded in a memory of the system. Multiple sessions can be monitored to build a patient history, providing the patient reactions under specific conditions. These recorded adjustments and parameters may be analyzed to determine a most appropriate adjustment(s) for a particular patient. The recorded adjustments and parameters can be saved in a machine readable storage medium as a patient history or profile that can be used by the system in subsequent dialysis sessions. The processor or computing unit can receive the dialysis results from a previous session, as well as the dialysis prescription from the previous session, including any intra-cycle changes to the osmotic agent concentration, as well as the timing of the intra-cycle changes. Based on the dialysis results and the dialysis prescription, the system can determine the timing and type of changes preferred for subsequent sessions. For example, if the patient responded well to a single mid-cycle adjustment increasing the osmotic agent concentration in a previous session, the system can utilize the same prescription in a subsequent session. If the patient responded poorly to a single mid-cycle adjustment, the system can employ a new dialysis prescription including multiple mid-cycle adjustments or by changing the timing of the mid-cycle adjustments. The timing of the intra-cycle adjustment is not limited to mid-cycle and can include any time point during the cycle. For example, the step of infusing the concentrated osmotic agent solution into the patient can occur at any time point during a cycle, e.g., $\frac{1}{16}$, $\frac{1}{8}$, $\frac{1}{4}$, $\frac{1}{2}$, $\frac{7}{8}$, $\frac{3}{4}$, $\frac{15}{16}$ of a cycle. Similarly, infusing the sterile fluid into the peritoneal cavity to adjust the concentration downward can occur at any time point during a cycle, e.g., $\frac{1}{16}$, $\frac{1}{8}$, $\frac{1}{4}$, $\frac{1}{2}$, $\frac{7}{8}$, $\frac{3}{4}$, $\frac{15}{16}$ of a cycle, to increase transport effectiveness at any point during a cycle. T the system can also consider other physiologic parameters when determining a specific profile to use. For example, the system can consider patient weight gain to determine the volume of fluid needed to remove. Various profiles may be more suitable for different starting conditions. Patient blood pressure and the time since the last dialysis session are other parameters that could be considered. Any patient parameter can be used in determining the specific fluid removal profile to use.

Figure 2:
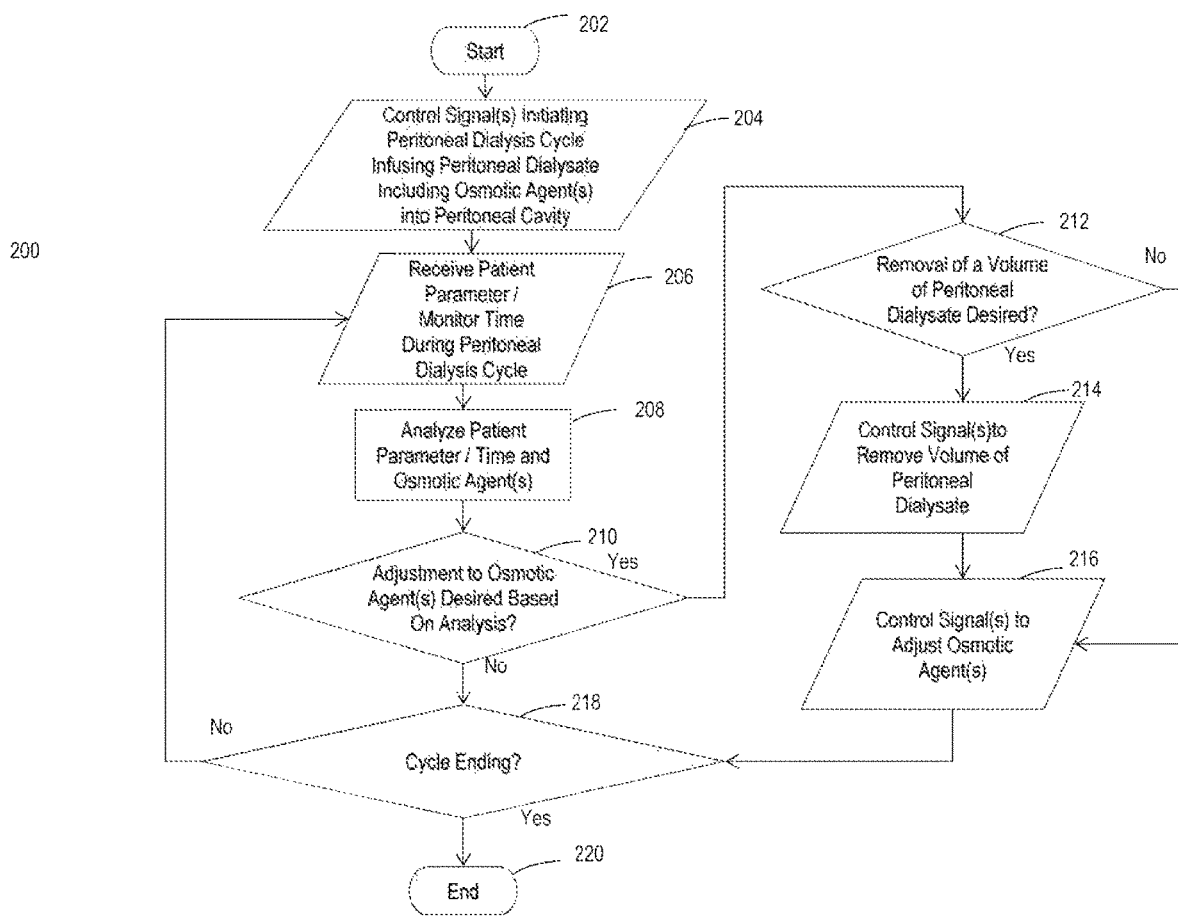
FIG. 2 shows a flow chart of a method for adjusting the osmotic agent concentration and dialysate volume within the peritoneal cavity of a patient.

FIG. 2 is a flowchart of a computer implemented method 200 for adjusting an osmotic agent concentration in a peritoneal cavity of a patient. The method can be performed using a system programmed or constructed to adjust an osmotic agent concentration in a peritoneal cavity of a patient. The system can include a machine readable storage medium including instructions that, when executed by a dialysis machine, cause the dialysis machine and related components to perform any one of the described methods.

The method 200 can begin in operation 202. In operation 204, one or more control signals initiating a peritoneal dialysis cycle may be issued by the processor of the system. The control signals may cause peritoneal dialysate including one or more osmotic agents to be infused through the infusion line into a peritoneal cavity of the patient thereby delivering an initial bolus of fluid. For example, a processor of the system can be in communication with the concentrate source and osmotic agent sources and can control the movement of fluid from the concentrate source and osmotic agent sources to a peritoneal dialysate generation flow path of the system. The processor of the system can control the movement of peritoneal dialysate into the peritoneal cavity. The method 200 may proceed to operation 206.

In operation 206, a parameter (such as time or a patient parameter) may be received or monitored by the system. For example, a duration of time passed since infusion of the peritoneal dialysate into the peritoneal cavity of the patient may be monitored by the processor to adjust the osmotic agent concentration at a set time after infusion of the peritoneal dialysate. The set time can be any time between infusion of the initial peritoneal dialysate and drainage of the peritoneal dialysate, including at $\frac{1}{8}$, $\frac{1}{4}$, $\frac{1}{3}$, $\frac{1}{2}$, $\frac{2}{3}$, $\frac{3}{4}$, $\frac{5}{8}$, or $\frac{7}{8}$ of the way through the cycle, or any combination thereof. Additionally or alternatively, one or more patient parameters may be received during the current cycle. For example, the processor of the system can monitor one or more patient parameters while the peritoneal dialysate is inside the peritoneal cavity during the current cycle. For example, a blood pressure of the patient may be sensed by a blood pressure sensor and monitored by the processor of the system. Additionally, the intraperitoneal pressure of the patient can be sensed and monitored. The method may proceed to operation 208.

In operation 208, parameters of operation 206 and the amount and/or type of osmotic agents in the peritoneal dialysate when the cycle was initiated may be analyzed. For example, a patient parameter such as blood pressure and/or the osmotic agent concentration of the fluid initially infused into the peritoneal cavity of the patient may be analyzed. As another example, the duration of time passed since infusion of the peritoneal dialysate may be analyzed. The method may proceed to operation 210.

In operation 210, a determination may be made regarding whether an adjustment to the osmotic agent concentration in the peritoneal cavity of the patient is desirable based on the analysis of operation 208. For example, if the patient's blood pressure indicates the patient is experience a hypotensive episode, a determination may be made to dilute the osmotic agent in the peritoneum cavity by controlling the flow of fluid from a the water source into the peritoneal dialysate generation flow path and into the patient. As another example, if a predetermined period of time has passed since the initial infusion of the peritoneal dialysate, the system may determine that a "spike" the fluid in the peritoneal cavity by adding glucose and/or dextrose is desired. If during operation 210, a determination is made that an adjustment to the osmotic agent concentration is desirable, the method 200 may proceed to operation 212. If during operation 210, a determination is made that an adjustment to the osmotic agent concentration is desirable, the method 200 may proceed to operation 212.

In operation 212, a determination may be made regarding whether removal of a volume of peritoneal dialysate from the peritoneal cavity of the patient is desired. For example, in the example where a determination is made to dilute the osmotic agent in the peritoneum by controlling sterile fluid from the water source, draining a volume of peritoneal dialysate from the peritoneal cavity to maintain overall cycle volume and avoid overfilling when adding new fluid may be desirable. In the example where a determination is made to "spike" the fluid in the peritoneal cavity by adding a bolus of concentrated osmotic agent solution, draining a volume of peritoneal dialysate from the peritoneal cavity to avoid overfilling when adding new fluid may be desired. Pressure sensors can be included in the cycler to determine the fullness of the patient prior to infusing new fluids.

If, during operation 212, a determination is made that draining a volume of peritoneal dialysate is desired, the method 200 may proceed to operation 214. In operation 214, one or more control signals causing drainage of some of the fluid in the peritoneal cavity may be issued by the processor of the system. The method may proceed to operation 216. If during operation 212, a determination is made that draining a volume of peritoneal dialysate is not desired, the system may proceed to operation 216.

In operation 216, one or more control signals may be sent to components of the system to adjust the osmotic agent concentration of the peritoneal dialysate in the peritoneal cavity of the patient by infusing a sterile fluid into the peritoneal cavity by selectively flowing fluid from one or more concentrate sources into the patient. For example, the processor of the system may control the movement of concentrate solution from one or more concentrate sources to the peritoneal dialysate generation flow path. Additionally or alternatively, the processor of the system may control the movement of one or more osmotic agents from one or more osmotic agent sources to the peritoneal dialysate generation flow path. Additionally or alternatively, the processor of the system may control the movement of fluid from, e.g., a water source to the peritoneal dialysate generation flow path. Additionally or alternatively, the processor of the system may control the movement of peritoneal dialysate into the peritoneal cavity of the patient through an infusion line.

The system can additionally employ a learning mode. When the patient first utilizes the system, the system can trial various osmotic agent bolus timings to determine the most appropriate for the patient and patient state. The delivery of an osmotic agent bolus "spikes" the peritoneal dialysate with osmotic agent. Various parameters in a given cycle can be varied and recorded. Parameters such as bolus amount, bolus timing, and the number of boluses can be recorded. Performance criteria can include the volume of ultrafiltrate removed and toxin concentration of the effluent. The number of bolus applications can vary between 1 and 5; amount between 10% and 50% of the initial fill volume. The effluent concentration can be evaluated by any techniques known in the art, including any of the sensors.

Figure 3:
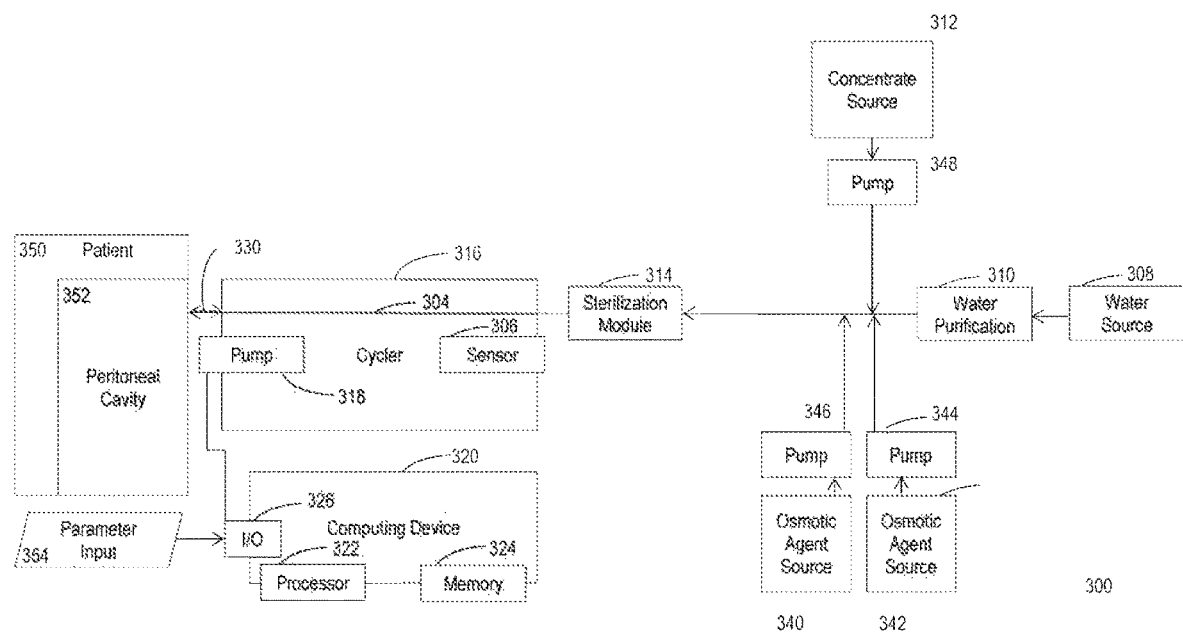
FIG. 3 shows a system for adjusting the osmotic agent concentration within the peritoneal cavity of a patient.

FIG. 3 illustrates an on-line peritoneal dialysis machine 300 for adjusting an osmotic agent concentration in a peritoneal cavity 352 of a patient mid-cycle. The system 300 can include a combined peritoneal dialysate effluent line and infusion line 330, referred to herein as an infusion line, a peritoneal dialysate generation flow path 304, at least one sensor 306, a peritoneal dialysis cycler 316, and a computing device 320. The system 300 can be embodied an integrated cycler wherein the peritoneal dialysis cycler 316 includes the peritoneal dialysate infusion line 330, the peritoneal dialysate generation flow path 304, and the at least one sensor 306 thereby forming the on-line peritoneal dialysis machine 300 for adjusting an osmotic agent concentration a peritoneal cavity 352. Although shown as a combined effluent and infusion line 330, one of skill in the art will understand that separate effluent and infusion lines can be used. Alternatively, the peritoneal dialysis cycler 316 can be nonintegrated without the peritoneal dialysate generation flow path 304. The computing device 320 can be a part of the peritoneal dialysis cycler 316, whether integrated or nonintegrated, or can be separate device in communication with the components of the present invention.

The peritoneal dialysate generation flow path 304 can include a water source 308, one or more water purification modules 310, a concentrate source 312, one or more osmotic agent sources 340, 342, a sterilization module 314, and the peritoneal dialysis cycler 316. The concentrate source 312 and/or osmotic agent sources 340, 342 can contain one or more solutes. The water source 308, water purification module 310, concentrate source 312, osmotic agent sources 340, 342, sterilization module 314, and peritoneal dialysis cycler 316 can be fluidly connectable to the peritoneal dialysate generation flow path 304. The peritoneal dialysis cycler 316 can include the infusion line 330, and one or more infusion pumps 318 for infusing peritoneal dialysate into the peritoneal cavity 352 of the patient 350 and draining fluid from the peritoneal cavity 352 of the patient 350. One or more processors 322 can adjust an osmotic agent concentration for a current or subsequent cycle of the peritoneal dialysis session. For example, the processor 322 can adjust the movement of osmotic agent solution from the osmotic agent sources 340, 342 to the peritoneal dialysate generation flow path 304.

The water source 308 can be a non-purified water source, such as tap water, wherein the water from the water source 308 can be purified by the system. A non-purified water source can provide water without additional purification, such as tap water from a municipal water source, water that has undergone some level of purification, but does not meet the definition of "purified water" provided, such as bottled water or filtered water. The water source can contain water meeting the WHO drinkable water standards provided in Guidelines for Drinking Water Quality, World Health Organization, Geneva, Switzerland, 4th edition, 2011. Alternatively, the water source 308 can be a source of purified water, meaning water that meets the applicable standards for use in peritoneal dialysis without additional purification. The system pumps water from the water source to the water purification module 310 to remove chemical contaminants in the fluid in preparation of the dialysate. The water purification module 310 can be a sorbent cartridge containing anion and cation exchange resins and/or activated carbon.

The system can pump the fluid to a sterilization module 314 for sterilization of the peritoneal dialysate prior to infusion into the patient. The sterilization module 314 can include one or more of a first ultrafilter, a second ultrafilter, and a UV light source, or any combination thereof. The sterilization module can be any component or set of components capable of sterilizing the peritoneal dialysate.

The concentrate source 312 and/or osmotic agent sources 340, 342 can contain one or more solutes for generation of the peritoneal dialysate from purified water. The concentrates in the concentrate source 312 and osmotic agent sources 340, 342 are utilized to create a peritoneal dialysis fluid that matches a dialysis prescription. A concentrate pump 348 and osmotic agent pumps 344, 346 in communication with the processor or computing unit controls the movement of concentrates and osmotic agents from the concentrate source 312 and osmotic agent sources 340, 342 into the peritoneal dialysate generation flow path 304. Table 2 provides non-limiting exemplary ranges of commonly used components of peritoneal dialysate. One of skill in the art will understand that alternatives to the components listed in Table 2 can be used. Other osmotic agents can be used in addition to, or in place of, the dextrose, including icodextrine or amino acid solutions, including dialysate with multiple osmotic agents. Further, when infusing concentrated osmotic agent into the peritoneal cavity of the patient, the system can use an osmotic agent concentration significantly higher than shown in FIG. 2. Although the sources of sodium, calcium, and magnesium listed in Table 2 are chloride salts, other sodium, magnesium, and calcium salts can be used, such as lactate or acetate salts. Peritoneal dialysate may also contain buffers for maintaining pH of the peritoneal dialysate. Exemplary, non-limiting examples of suitable buffers include bicarbonate buffer, acetate buffer or lactate buffer. Although not generally used in peritoneal dialysis, potassium chloride can be used for hypokalemic patients who don't receive sufficient potassium through diet. The concentrate sources 312 and osmotic agent sources 340, 342 can include any number of concentrates and/or osmotic agents combined or in separate sources. For example, one or more osmotic agent sources 340, 342 can be included in addition to a single ion concentrate source. Alternatively, multiple ion concentrate sources can be used with each ion concentrate in a separate concentrate source. Any combination of concentrates and/or osmotic agents in any number of sources can be used with the invention.

TABLE 2

| Component | Concentration |
|---|---|
| Sodium chloride | 132-134 mmol/L |
| Calcium chloride dehydrate | 1.25-1.75 mmol/L |
| Magnesium chloride hexahydrate | 0.25-0.75 mmol/L |
| Sodium Lactate | 35-40 mmol/L |
| Dextrose (D-glucose) monohydrate | 0.55-4.25 g/dL |

TABLE 2-continued

| Component | Concentration |
|---|---|
| pH | 5-6 |
| Osmolality | 346-485 (hypertonic) |

The system can use multiple osmotic agent sources 340, 342 containing different osmotic agents. For example, a first osmotic agent source 340 can contain glucose, while a second osmotic agent source 342 can contain icodextrine. Glucose provides a fast transport while icodextrine provides transport over a longer period of time. The system can use both glucose and icodextrine in a single cycle to give better results over the entire cycle length. Additionally, the system can use the glucose in overnight sessions and use icodextrine in the last CAPD (day) cycle to give a good long transport. For the last cycle within the session, the system can optionally use icodextrine to provide a slow and long acting exchange for a daytime CAPD session. The concentrate sources can infuse each particular concentrate to provide an infused ion concentration that is lower than a prescribed amount for a particular patient. One desired outcome can be to provide a concentration for a particular ion that is lower than a patient's pre-dialysis ion concentration. Additionally, if multiple ion sources are to be delivered by a concentrate source, the present system can selectively dilute a desired ion while maintaining concentration levels for other ions. Hence, the present invention can avoid adjusting down every ion insofar as an added diluent may adversely affect concentrations of ions already in a normal range.

The water source 308, water purification module 310, concentrate source 312, osmotic agent sources 340, 342, and sterilization module 314 can be fluidly connectable to the peritoneal dialysis cycler 316 for immediate delivery of the generated peritoneal dialysate to the patient. Alternatively, a peritoneal dialysate reservoir (not shown) can be included to collect the generated peritoneal dialysate for later use. One or more processors 322 which can be part of a larger computing device 320, can control the movement of fluid from the concentrate source 312 osmotic agent sources 340, 342 to the peritoneal dialysate generation flow path 304, for example, by controlling the pumps 344, 346, 348. The processors 322 can also control one or more pumps 318 in the cycler and a heater (not shown) for heating the peritoneal dialysate prior to infusion. One or more sensors can be included in the peritoneal dialysate generation flow path 304 and/or the infusion line 330 to ensure the therapy delivered to the patient matches a peritoneal dialysate prescription.

Patient parameters can be monitored by the one or more sensors 306. Patient parameters can also be derived from the patient 350 such as by monitoring blood pressure via a sensor 306 monitoring the patient 350. Patient parameters can also be input into the system 300 as a parameter input 354. A sensor 306 can be positioned in the peritoneal dialysate effluent line 302, the peritoneal dialysate generation flow path 304, or in both the peritoneal dialysate effluent line 302 and the peritoneal dialysate generation flow path 304. A sensor 306 can be connected to the patient 350. For example, a blood pressure sensor can be connected to the patient 350. Patient parameters can be derived using the one or more or more sensors 306. Implantable sensors or wearable sensors, such as implantable cardiac rhythm management systems or other sensors can be in communication with the processors 322 to provide the system with patient parameters. The sensors 306 can be separate sensors, a combined sensor positioned along both the peritoneal dialysate infusion line 330 and the peritoneal dialysate generation flow path 304, or combined or separate sensors along a common peritoneal dialysate infusion line and peritoneal dialysate generation flow path. The sensors 306 can be placed at various locations along the peritoneal dialysate infusion line 330 and the peritoneal dialysate generation flow path 304, including within or between the cycler 316, the water source 308, the water purification module 310, the concentrate source 312, the osmotic agent sources 340, 342, and the sterilization module 314, or between the cycler 316 and the peritoneal cavity 352. The sensors 306 can be posited to take measurements directly from the patient 350.

The one or more sensors 306 can include blood pressure sensor to measure blood pressure of a patient 350 during a cycle. The sensor 306 can include a flow sensor to measure a volume of fluid infused and/or removed from a peritoneal cavity 352 of the patient 350. The sensor 306 can include a solute concentration sensor to measure a solute concentration of the fluid infused and/or removed from the patient. The sensor 306 can include a refractive index sensor to measure glucose or other osmotic agent concentration in fluid infused and/or removed from the patient. The sensor 306 can include a conductivity sensor or ion selective electrodes to measure conductivity or solute concentration of fluid infused and/or removed from the patient. The sensor 306 can include a pressure sensor to measure a pressure of fluid infused and/or removed from a patient. The sensor 306 can include a temperature sensor to measure a temperature of fluid infused and/or removed from a patient.

The computing device 320 can include the one or more processors 322, memory 324, and one or more input/output interfaces 326. One of ordinary skill in the art will recognize that the memory 324 can include long-term memory and operating memory, and/or memory serving as both long-term memory and operating memory. The memory 324 can be a machine-readable storage medium. The memory 324 can be in communication with the processor 322 and store instructions that when executed perform methods. The input/output interfaces 326 can include an input interface to receive parameter input 354, an input port to receive information from the one or more sensors 306, and an output port to output control signals adjusting an osmotic agent concentration in a peritoneal cavity 352 of a patient. The processor 322 can be in communication with the at least one sensor 306. As with all features of the present application, intervening components (such as the input/output interface 326) can be present between the processor 322 and the sensor 306. The computing device 320 can be a stand-alone device independent of the peritoneal dialysis cycler 316, or can be a part of peritoneal dialysis cycler 316. The computing device 320 can be a remote device in network communication with the sensor 306, such as via the Internet.

An alternative system for monitoring patient parameters during a peritoneal dialysis session to make modifications within the peritoneal dialysis session can include a peritoneal dialysate regeneration module. An infusion line can be fluidly connected to a peritoneal dialysate generation flow path downstream of a sterilization module. A peritoneal dialysate effluent line can be fluidly connected to the peritoneal dialysate generation flow path upstream of the peritoneal dialysate regeneration module. The peritoneal dialysate regeneration module can include a sorbent cartridge, an electrodialysis unit, one or more ultrafilters, or any other combination of components for removal of contaminants from the dialysate removed from the patient. The used peritoneal dialysate, after regeneration, can be pumped back into the peritoneal dialysate generation flow path for reuse.

Prophetic Example 1

Figure 4:
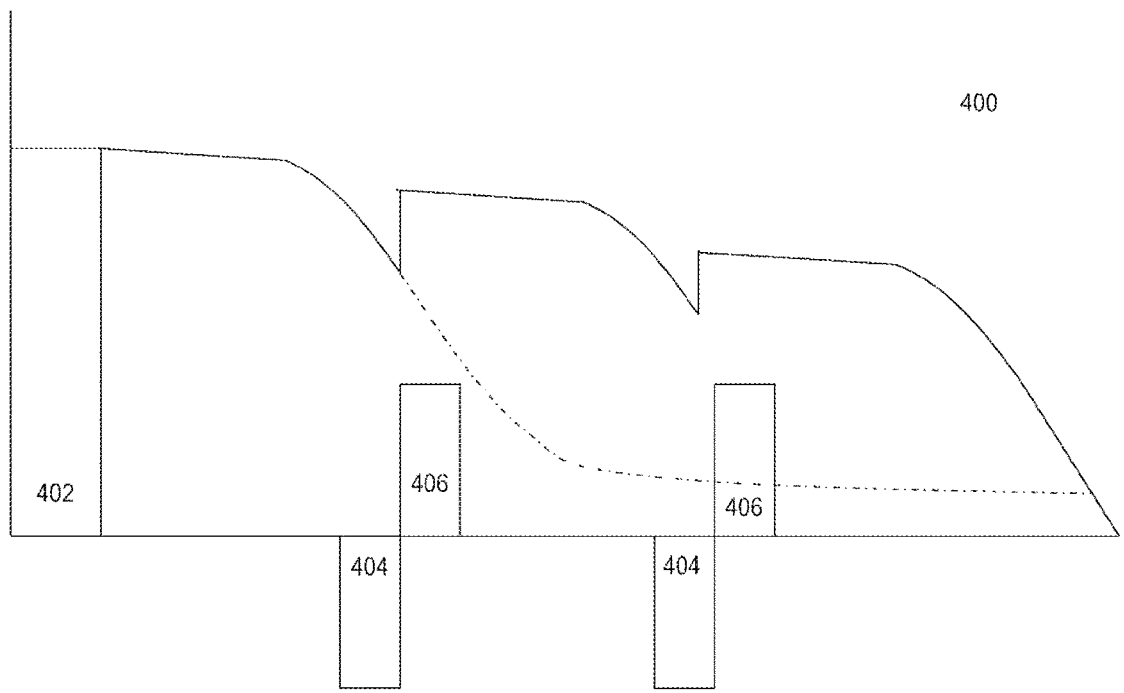
FIG. 4 is a graphical representation of prophetic changes to dialysate made within the peritoneal cavity of a patient.

The chart of FIG. 4 shows a prophetic example of infusion periods. For example, if during operation 210 of FIG. 2, a determination is made that an adjustment to the osmotic agent concentration is not desirable, the method 200 may proceed to operation 218. In operation 218, a determination can be made regarding whether the current cycle is ending. If during operation 218, a determination is made that the current cycle is not ending, the method 200 may proceed to operation 206, where a parameter may be received or monitored by the system. If during operation 218, a determination is made that the current cycle is ending, the method 200 may proceed to operation 220 and end.

In FIG. 4, the graph shows a peritoneal dialysis cycle 400. With the on-line peritoneal dialysate fluid generation system illustrated in FIG. 3, the osmotic agent can be delivered in a more even manner throughout each cycle. The initial bolus of peritoneal dialysate fluid introduced at the beginning of each cycle can have a lower osmotic agent concentration. Then, periodically throughout the cycle, additional high concentrations of osmotic agent can be introduced to boost and create a more even transfer profile. The chart shows a prophetic transport effectiveness of a peritoneal cavity (solid line) when modified through osmotic agent customization. The chart also shows a prophetic transport effectiveness when not modified (dashed line). During the initial bolus of fluid 402 and immediately after, the modified effectiveness and the unmodified effectiveness are identical or similar. However, after a draining of a volume of fluid 404 and infusion of subsequent bolus of fluid 406, the modified effectiveness is increased due to the spike in osmotic agents.

For each cycle, an initial bolus of fluid 402 equivalent to that generally used in peritoneal dialysis, or between 1.5 and 3 L, can be used but can be infused with less osmotic agent than traditional systems. The amount can be variable and could vary from a typical amount to ⅓ or less. Then, at predefined times, depending on the decay of the osmotic effect, a bolus of fluid and osmotic agent can be added to enhance the therapeutic effect. A portion of the peritoneal dialysate in the peritoneal cavity of the patient can be drained to compensate for the added bolus, and the amount removed could be equivalent to the amount being added (10-50% of initial volume) to maintain overall cycle volume. Removal of a portion of the peritoneal dialysate can also maintain patient comfort, as too much fluid in the peritoneal cavity can distend the belly and feel uncomfortable for the patient.

One skilled in the art will understand that various combinations and/or modifications and variations can be made in the described systems and methods depending upon the specific needs for operation. Moreover, features illustrated or described as being part of an aspect of the invention may be used in the aspect of the invention, either alone or in combination.

We claim:

1. A method, comprising the steps of:
adjusting an osmotic agent concentration of peritoneal dialysate in the peritoneal cavity of a patient during a cycle by infusing a concentrated osmotic agent solution or by infusing sterile fluid into the peritoneal cavity of the patient by infusing the peritoneal dialysate into the peritoneal cavity of the patient at a beginning of the cycle and adjusting the osmotic agent concentration by selectively flowing fluid from an osmotic agent source or a sterile fluid source into the peritoneal cavity of the patient at a set time after infusing the peritoneal dialysate into the peritoneal cavity of the patient.

2. The method of claim 1, further comprising the step of draining a volume of peritoneal dialysate from the peritoneal cavity of the patient prior to the step of infusing the concentrated osmotic agent solution or infusing the sterile fluid into the peritoneal cavity of the patient.

3. The method of claim 1, further comprising the step of receiving one or more patient parameters during the cycle.

4. The method of claim 3, further comprising the step of determining a change to the osmotic agent concentration of the peritoneal dialysate in the peritoneal cavity of the patient based on the one or more patient parameters prior to the step of adjusting the osmotic agent concentration.

5. The method of claim 4, wherein the patient parameters are selected from the group of: blood pressure; and inter-peritoneal pressure.

6. The method of claim 4, further comprising the steps of determining an intraperitoneal pressure at a first time and at least a second time, and wherein the step of determining a change to the osmotic agent concentration comprises determining a change to the osmotic agent concentration based on a change in intraperitoneal pressure.

7. The method of claim 3, wherein the steps of receiving the one or more patient parameters, and adjusting the osmotic agent concentration of the peritoneal dialysate are performed by a processor of an on-line dialysis machine.

8. The method of claim 7, wherein the patient parameters are received by the processor while the peritoneal dialysate is inside the patient during the cycle.

9. The method of claim 1, wherein the step of adjusting the osmotic agent concentration comprises selectively flowing fluid from an osmotic agent source into the peritoneal cavity of the patient.

10. The method of claim 9, wherein the osmotic agent source contains glucose, dextrose, icodextrin, or combinations thereof.

11. The method of claim 1, wherein the peritoneal dialysate comprises multiple osmotic agents.

12. The method of claim 11, wherein the peritoneal dialysate comprises icodextrin and either glucose or dextrose.

13. The method of claim 1, further comprising the steps of draining the peritoneal dialysate from the patient; and infusing a second peritoneal dialysate into the patient; wherein the second peritoneal dialysate comprises an osmotic agent different from the first peritoneal dialysate.

14. The method of claim 1, further comprising the steps of:
receiving one or more dialysis results from at least one prior dialysis session into a machine readable storage medium; and receiving a dialysis prescription from the prior dialysis session into a machine readable storage medium;
wherein the one or more dialysis results includes a volume of ultrafiltrate removed and a rate of ultrafiltration and wherein the dialysis prescription comprises an adjustment made to the osmotic agent concentration in the peritoneal cavity of the patient during the prior dialysis session.

15. The method of claim 14, wherein the step of adjusting the osmotic agent concentration comprises determining a change to the osmotic agent concentration based on the dialysis results from the prior dialysis session and the dialysis prescription from the prior dialysis session.

16. The method of claim 1, wherein the method is performed by an on-line dialysis machine.

17. The method of claim 1, wherein the step of infusing the concentrated osmotic agent solution into the patient is performed mid-cycle.

18. The method of claim 1, wherein the step of infusing the sterile fluid into the peritoneal cavity of the patient is performed mid-cycle.

* * * * *